US 9,358,020 B2

(12) United States Patent
Smith (10) Patent No.: US 9,358,020 B2
(45) Date of Patent: Jun. 7, 2016

(54) CATHETER DEVICE FOR DELIVERY ENERGY TO A VEIN

(75) Inventor: Scott Smith, Chaska, MN (US)

(73) Assignee: BOSTON SCIENTIFIC SCIMED INC., Maple Grove, MN (US)

( * ) Notice: Subject to any disclaimer, the term of this patent is extended or adjusted under 35 U.S.C. 154(b) by 941 days.

(21) Appl. No.: 13/168,724

(22) Filed: Jun. 24, 2011

(65) Prior Publication Data
US 2011/0319809 A1 Dec. 29, 2011

Related U.S. Application Data (60) Provisional application No. 61/358,715, filed on Jun. 25, 2010.

(51) Int. Cl.
| *A61B 17/22* | (2006.01) |
|---|---|
| *A61B 18/14* | (2006.01) |
| *A61B 5/04* | (2006.01) |
| *A61B 18/00* | (2006.01) |
| *A61B 18/18* | (2006.01) |
| *A61M 25/10* | (2013.01) |
| *A61N 1/05* | (2006.01) |
| *A61B 17/00* | (2006.01) |

(52) U.S. Cl.
CPC .............. *A61B 17/22* (2013.01); *A61B 18/1492* (2013.01); *A61B 5/04001* (2013.01); *A61B 17/00008* (2013.01); *A61B 2017/22061* (2013.01); *A61B 2017/22097* (2013.01); *A61B 2018/0022* (2013.01); *A61B 2018/00023* (2013.01); *A61B 2018/00291* (2013.01); *A61B 2018/00404* (2013.01); *A61B 2018/00839* (2013.01); *A61B 2018/1861* (2013.01); *A61M 25/1027* (2013.01); *A61M 2025/105* (2013.01); *A61M 2025/1086* (2013.01); *A61N 1/056* (2013.01)

(58) Field of Classification Search
CPC ...................... A61B 2562/0219; A61B 5/0452; A61B 5/01; A61B 17/3417; A61B 18/24; A61B 17/00008; A61B 17/22; A61B 18/1492; A61B 2017/22061; A61B 2017/22097; A61B 2018/00023; A61B 2018/0022; A61B 2018/00291; A61B 2018/00404; A61B 2018/00839; A61B 2018/1861; A61B 5/04001; A61M 2205/3592; A61M 2025/1086; A61M 2025/105; A61M 37/00; A61M 5/14; A61M 25/10; A61M 25/1027; A61N 1/056
USPC ................. 606/158, 32, 194; 604/21; 607/115
See application file for complete search history.

(56) References Cited

U.S. PATENT DOCUMENTS

| 2004/0098030 | A1* | 5/2004 | Makower et al. | ............. 606/200 |
|---|---|---|---|---|
| 2009/0137968 | A1* | 5/2009 | Rottenberg | .................... 604/264 |
| 2009/0299421 | A1* | 12/2009 | Sawchuk | .......................... 607/4 |
| 2010/0160905 | A1* | 6/2010 | Shadduck | ....................... 606/27 |

* cited by examiner

*Primary Examiner* — Kami A Bosworth
*Assistant Examiner* — Brandy S Lee
(74) *Attorney, Agent, or Firm* — Seager, Tufte & Wickhem LLP (57) ABSTRACT

The present disclosure relates to devices, systems, and methods associated with a catheter device for delivering energy to a vein. One or more catheter devices include a cooling device, an infusion device, and an energy delivery device for delivering energy to a vein to treat incompetent valves.

20 Claims, 9 Drawing Sheets

CATHETER DEVICE FOR DELIVERY ENERGY TO A VEIN

PRIORITY INFORMATION

This application claims priority to U.S. Provisional Application 61/358,715 filed Jun. 25, 2010, the specification of which is incorporated herein by reference.

TECHNICAL FIELD

The present disclosure relates generally to catheter devices, systems, and methods, and more particularly to catheter devices for delivering energy to a vein.

BACKGROUND

The venous system contains numerous one-way valves for directing blood flow back to the heart. Venous valves contain leaflets, with each leaflet forming a reservoir for blood which, under retrograde blood pressure, forces the free surfaces of the leaflets together to prevent retrograde flow of the blood and allow antegrade blood flow to the heart. When a valve becomes incompetent, the leaflets of the valve are unable to close because the leaflets fail to form a proper seal and retrograde flow of the blood cannot be stopped. Incompetent valves increase the strain and pressure that occurs within the lower venous sections and overlying tissues, sometimes leading to additional venous valve failure.

One particular condition that results from incompetent valves is varicose veins. Varicose veins often involve incompetence of one or more venous valves. Venous valve incompetence allows reflux of blood within the venous system and can cause dilation and tortuosity of veins, particularly within the superficial veins of the lower limbs. Besides cosmetic problems, varicose veins can be painful, especially when standing or walking. Additionally, varicose veins can cause discoloration, itching, and swelling. If left untreated, varicose veins may cause medical complications such as bleeding, phlebitis, ulcerations, thrombi, and lipodermatosclerosis.

Treatment of varicose veins includes both non-surgical and surgical treatments. Non-surgical treatments include, elastic stockings, elevating the legs, and exercise. While providing temporary relief, non-surgical treatments do not correct the underlying medical issue, which is the incompetent valve. Surgical treatments for varicose veins include vein stripping, ambulatory phlebectomy, vein-segment transplant, and thermal ablation. Thermal ablation includes delivering energy, e.g. radio frequency (RF) energy, to the vein to remove the incompetent valve from circulation by occluding the vein. While effective in treating the incompetent valve, thermal ablation involves many injections along the length of the vein to be treated and can be painful and time-consuming. Additional drawbacks with thermal ablation include the risk of damaging surrounding tissue.

DETAILED DESCRIPTION

The present disclosure relates generally to catheter devices, systems, and methods associated with delivering energy to a vein. In one or more embodiments, a catheter device can be used to treat incompetent veins in the body, e.g. superficial veins in the lower limbs, among others, that have become varicose. Superficial veins, which return only about 10 percent (%) of the total blood of the legs, can be removed from circulation without harm to the patient. Herein, particular discussion is made to the treatment of varicose veins in the legs; however, the catheter device of the present disclosure can be used for treating veins in other areas of the body.

The figures herein follow a numbering convention in which the first digit or digits correspond to the drawing figure number and the remaining digits identify an element or component in the drawing. Similar element or components between different figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide any number of additional embodiments of a catheter device and/or system. In addition, as will be appreciated the proportion and the relative scale of the elements provided in the figures are intended to illustrate the embodiments of the present invention, and should not be taken in a limiting sense.

Embodiments of the present disclosure are illustrated in the figures. Generally, the catheter device can be inserted within a fluid passageway of a body lumen, e.g. a vein, for treatment of an incompetent valve that has become varicose, to delivery energy to the vein. The delivered energy can help collapse the vein, which restricts the blood flow through the vein thereby potentially removing the incompetent valve from circulation.

For one or more embodiments, the catheter device of the present disclosure includes a cooling device, an infusion device, and an energy delivery device. The catheter device can be advanced within the vein to treat the incompetent valve that may have become varicose. The catheter device including the cooling device, infusion device, and energy delivery device can be used to treat the vein while minimizing the pain felt by the patient and the overall time for the treatment.

For example, the cooing device can be used to reduce a temperature of the vein, which can affect transmission of impulses from nerves of the vein and cause a decreased sensitivity of the nerves. The decreased sensitivity of the nerves provides pain relief while an anesthetic fluid is delivered to a perivenous location. Additionally, the anesthetic fluid can further decrease the sensitivity of the nerves of the vein to provide pain relief while energy is being delivered to the vein.

One or more embodiments of the present disclosure further include a catheter device that includes a monitoring device. The monitoring device can monitor the transmission of impulses, i.e., electrical activity, of the nerves of the vein to monitor an amount of sensitivity lost in the nerves of the vein by the cooling device and/or the infusion device.

Vein ablation is a term used to describe a thermal treatment for occluding a vein, i.e., removing the vein from circulation. During vein ablation, energy is delivered to the vein by the energy delivery device. Applying energy to the vein causes a temperature of the vein to increase, which can help collapse the vein. Collapsing the vein reduces an initial diameter of the vein and can restrict the ability for blood flow through the vein, which can potentially remove the vein from circulation of the venous system.

For one or more embodiments, the catheter device and system can be used for, among other things, treatment of varicose veins. Additionally, the catheter device can be used to reduce the pain involved with vein ablation and delivery of the anesthetic fluid to the perivenous location, reduce the time of the overall treatment, and reduce the risk of damaging adjacent tissues.

Figure 1:
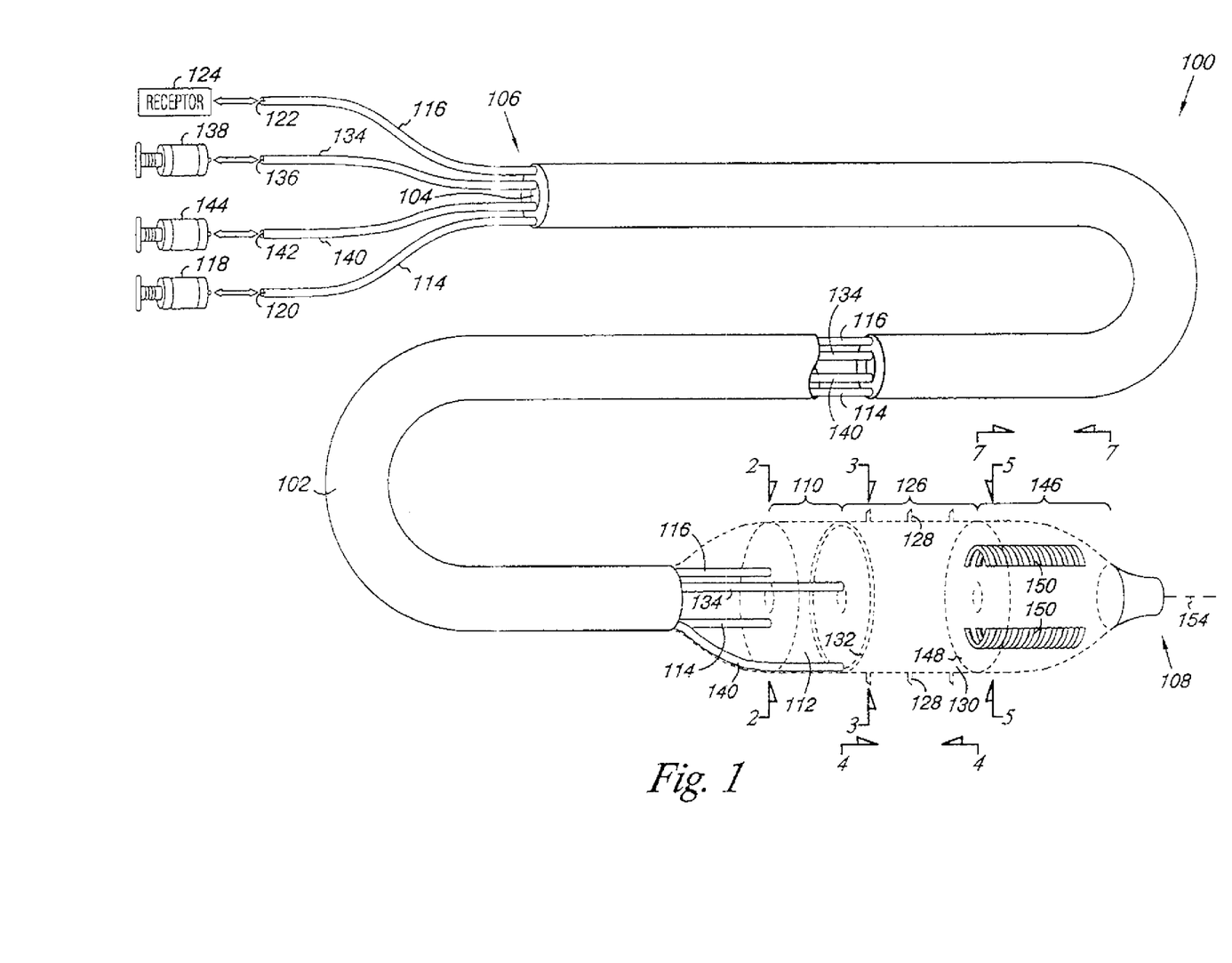
FIG. 1 illustrates an embodiment of a catheter device in accordance with one or more embodiments of the present disclosure.

FIG. 1 illustrates an embodiment of a catheter device in accordance with one or more embodiments of the present disclosure. For one or more embodiments, the catheter device 100 includes an elongate body 102 having a lumen 104. The elongate body 102 also includes a proximal end 106 and a distal end 108 relative to the point of introduction to the body. The elongate body 102 includes a cooling device 110 that is positioned towards the distal end 108 of the elongate body 102. The cooling device 110 includes a cooling balloon 112 and an inflow lumen 114 and an outflow lumen 116 to circulate a cooling fluid. The cooling balloon 112 is in fluid communication with the inflow lumen 114 to receive the cooling fluid from an inflation device 118. The inflow lumen 114 couples an inflation port 120 to an expandable volume defined at least in part by the cooling balloon 112.

The inflation device 118 can be releasably coupled to the catheter device 100, e.g. to the inflation port 120, from which the cooling fluid can be transferred under pressure to change an inflation state, e.g. an un-expanded state to an expanded state, of the cooling balloon 112. FIG. 1 illustrates an embodiment in which the cooling balloon 112 is in the expanded state.

For one or more embodiments, the cooling balloon 112 is in fluid communication with the outflow lumen 116 to allow for the cooling fluid to be circulated through the cooling balloon 112. The outflow lumen 116 couples a port 122 to a receptor 124 that collects the circulated cooling fluid. The port 120 and/or port 122 can include controls to maintain a pressure of the cooling balloon 112, a flow rate of the cooling fluid, and the inflation state of the cooling balloon 112. For one embodiment, the cooling fluid collected in the receptor 124 can pass through a cooling station (not shown) and be recirculated back through the cooling balloon 112 via the inflow lumen 114.

The cooling device 110, as illustrated in FIG. 1, includes the inflow lumen 114 and the outflow lumen 116 to circulate the cooling fluid through the cooling balloon 112. However, for one or more of the embodiments, the cooling balloon 112 can include a single lumen to deliver and remove the cooling fluid from the cooling balloon 110.

For one or more embodiments, the elongate body 102 further includes an infusion device 126. The infusion device 126 can be positioned adjacent the cooling device 112. The infusion device 126 includes at least one needle 128 that can puncture the vein to deliver an anesthetic fluid to the perivenous location. As seen in FIG. 1, the infusion device 126 includes more than one needle 128. The infusion device 126 can include an infusion balloon 130 and a chamber 132. The chamber 132 is in fluid communication with the needle 128 to deliver the anesthetic fluid to the perveinous location. For one or more embodiments, an inflation lumen 134 couples an inflation port 136 to an expandable volume defined at least in part by the infusion balloon 130 of the infusion device 126 of the elongate body 102.

An inflation device 138 can be releasably coupled to the catheter device 100, e.g. to the inflation port 136, to change the inflation state of the infusion balloon 130. FIG. 1 illustrates an embodiment in which the infusion balloon 130 is in the expanded state.

A lumen 140 can couple the chamber 132, which is in fluid communication with the needle 128, to a port 142. For the various embodiments, an inflation device 144 can be releasably coupled to the catheter device 100, e.g. to the port 142, to deliver the anesthetic fluid to the perivenous location via the needle 128.

Veins can naturally expand or stretch to approximately 500 percent (%) of their natural unloaded diameter. Thus, the expanded state of the infusion balloon 130 can account for the natural elastic stretching of the vein. As the infusion balloon 130 changes from the un-expanded state to the expanded state the pressure exerted from the needle 128 against the vein increases. Eventually, the needle 128 will puncture the vein. A length of the needle 128 can vary depending on the thickness and elasticity of the vein being treated.

Additional embodiments include an infusion balloon that has at least one slot on the side of the balloon that is configured to allow the needle to be passed through the slot. For example, the infusion balloon can be inflated to the expanded state so that the needle can pass through the slot and puncture the vein. The infusion device can further include a support, such as a metal braid and/or coil that can help stabilize the vein as the needle punctures the vein. Other infusion balloon designs that are configured to deliver the anesthetic fluid to a perivenous location can be used with the catheter device of the present disclosure.

For one or more embodiments, the elongate body 102 further includes an energy delivery device 146 to delivery energy to the vein. The energy delivery device 146 can be positioned adjacent the infusion device 126. For the embodiments, the energy delivery device 146 includes a body portion 148 and one or more electrodes 150 to delivery energy to the vein. As seen in FIG. 1, the energy delivery device includes two electrodes 150. The electrodes 150 can be partially or completely embedded in the body portion 148 of the energy delivery device 146. As seen in FIG. 1, the diameter of the energy delivery device 146 is illustrated as having a same diameter as the cooling device 110 and the infusion device 126. However, the diameter of the energy delivery device 146 can vary. For example, the profile and cross-section of the energy delivery device 146 can include various types of shapes and sizes, discussed further in connection with FIGS. 6 and 7A-7C.

Figure 11:
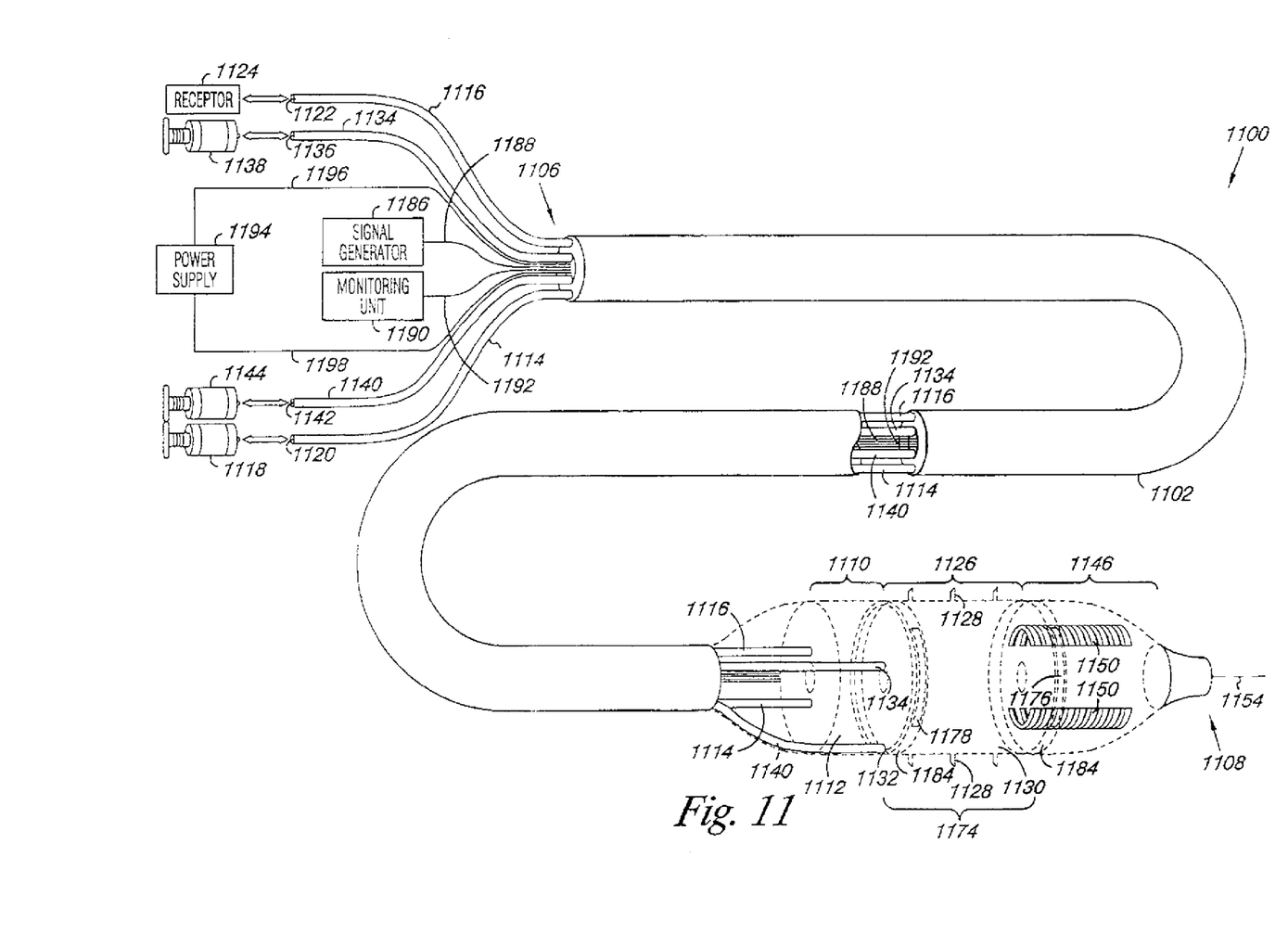
FIG. 11 illustrates an embodiment of the catheter device system according to the present disclosure.

For one or more embodiments, the electrodes 150 can be electrically coupled to a power supply, e.g. a RF generator, to deliver energy to the vein, discussed further in connection with FIG. 11. The power supply can be configured to provide energy to the vein such that the temperature of the vein increases and the vein beings to collapse. Although specific mention has been made regarding the energy delivery device applying RF energy to the vein, it is understood that other forms of energy such as microwaves, ultrasound, direct current, circulating a heated fluid, optical energy, radiant light, and lasers may be used. Additionally, thermal energy generated from a resistive coil may be used.

The energy delivery device can include electrodes 150 that can be in either a bipolar or a monopolar operation to deliver energy to the vein. For one or more embodiments, the RF energy is at a selected frequency within a range of from 350 milihertz (mHz) to 250 kilohertz (kHz). In another embodiment, the selected frequency can be within a range of from 5 kHz to 500 megahertz (MHz). In one embodiment, the selected frequency can be within a range of from 100 kHz to 1 MHz. Additionally, in one particular embodiment, the selected frequency can be 500 kHz. For microwaves, the selected frequency can be within a range from 1.0 gigahertz (GHz) to 5.0 GHz. In one embodiment, the selected frequency can be within a range of from 2.0 GHz to 2.5 GHz. Additionally, for infrared radiation, the wavelength can be within a range of from 500 nanometers (nm) to 1500 nm. The delivered energy can be converted into heat within the vein, and the thermal effect can cause the vein to collapse, thus reducing the initial diameter of the vein and restricting the flow of blood through the vein.

FIG. 1 provides an embodiment of the catheter device 100 where the cooling device 110, the infusion device 126, and the energy delivery device 146 are positioned sequentially along a longitudinal axis 154 of the elongate body 102. For one or more embodiments, the cooling device 110, infusion device 126, and energy delivery device 146 each have substantially the same length. For example, the cooling device 110, infusion device 126, and energy delivery device 146 each can have a length of from 3 millimeters (mm) to 6 mm. However, it is possible for the cooling device 110, infusion device 126, and energy delivery device 146 to each have varying lengths.

For the various embodiments, the catheter device can be formed from a suitable material, for example, but not limited to, polyoxymethylene, polybutylene terephthalate, polyether block ester, polyether block amide, fluorinated ethylene propylene, polyethylene, polypropylene, polyvinylchloride, polyurethane, polytetrafluoroethylene, polyether-ether ketone, polyimide, polyamide, polyphenylene sulfide, polyphenylene oxide, polysufone, nylon, polyether-ester, polymer/metal composites, or combinations thereof.

Figure 2:
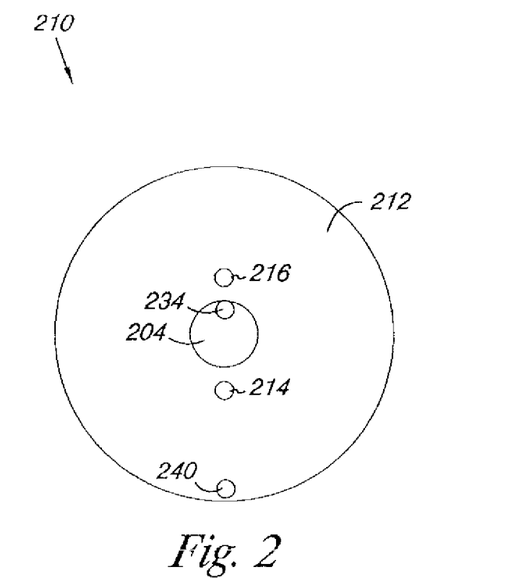
FIG. 2 illustrates a cross-sectional view of the catheter device illustrated in FIG. 1 taken along lines 2-2.

FIG. 2 illustrates a cross-sectional view of the catheter device illustrated in FIG. 1 taken along lines 2-2. For one or more of the embodiments, the cooling device 210 can reduce a temperature of the vein by introducing and circulating the cooling fluid within the cooling balloon 212. As discussed above, the cooling fluid is delivered to the cooling balloon 212 via the inflow lumen 214 to change the inflation state from the un-expanded state to the expanded state. As the cooling balloon 212 inflates with the cooling fluid, the cooling balloon 212 can contact the vein and reduce the temperature of the vein. The cooling fluid can be removed from the cooling balloon 212 to circulate the cooling fluid via the outflow lumen 216.

Reducing the temperature of the vein can affect the transmission of impulses from the nerves and reduce the sensitivity of the nerves of the vein being treated. The reduced sensitivity can provide pain relief from the needles puncturing the vein to deliver the anesthetic fluid. Additionally, the cooling device can reduce a temperature of adjacent tissues external to the vein to provide thermal protection from the energy delivered from the energy delivery device.

For one or more of the embodiments, decreasing the temperature of the vein can include a cooling fluid, a pressure of the cooling balloon, a flow rate of the cooling fluid, and/or a contact time between the cooling balloon and the vein. Examples of the cooling fluid include, but are not limited to, ice slurry, cold water, alcohols, glycols, saline, hypertonic saline, dextrose solution, hyperosmotic glucose solutions, ethylene glycol solutions, mineral oils, vegetable oils, silicon oils, refrigerants, and combinations thereof. Examples of refrigerants include, but are not limited to, Freon®, carbon dioxide, argon, nitrous oxide, and propane. The vein temperature can be reduced to a temperature that desensitizes the nerves of the vein to help provide pain relief. In one embodiment, the temperature of the vein is reduced to 4 degrees Celsius (° C.). Depending on the choice of the cooling fluid, the contact time, the pressure of the cooling balloon, and the flow rate of the cooling fluid, the time to decrease the temperature of the vein to the temperature that desensitizes the nerves can vary. For one or more embodiments, the temperature of the cooling fluid can be within a range of from negative (−) 4 degrees ° C. to 4° C. Cooling the vein to temperatures within a range of 20° C. to 30° C. can desensitize the nerves of the vein. In one embodiment, the vein is cooled to a temperature within a range of −40° C. to −10° C. to freeze the vein. Freezing the vein can stabilize the vein, which can facilitate puncturing of the vein with needles of the infusion device.

Referring to FIG. 1, the pressure of the cooling balloon 112 and the flow rate of the cooling fluid can be controlled at port 120 and/or port 122 as the cooling fluid is circulated throughout the cooling balloon 112. For one or more embodiments, the pressure of the cooling balloon 112 can be within a range of from 1 pound per square inch (psi) to 500 psi. In embodiments, the pressure of the cooling balloon 112 can be within a range of from 10 psi to 100 psi. For one or more embodiments, the flow rate of the cooling fluid can be within a range of 0.1 milliliters per second (ml/s) to 5.0 ml/s. In embodiments, the flow rate of the cooling fluid is 1.0 rolls. For one or more embodiments, the cooling fluid is propane, the temperature of the propane is 0° C., and the pressure of the cooling balloon 112 is 50 psi.

For one or more of the embodiments, the cooling balloon can be formed from a suitable balloon material. For example, the cooling balloon can be formed from a semi-compliant material. Examples of semi-compliant materials include, but are not limited to, ethylene-vinyl acetate, polyvinyl chloride, olefin copolymers or homopolymers, polyethylenes, polyurethanes, crosslinked low density polyethylenes, highly irradiated linear low density polyethylene, acrylonitrile polymers and copolymers, acrylonitrile blends, ionomer resins, and combinations thereof. The cooling balloon can also be formed from a non-compliant material, for example, polyethylene terephthalates, polyacrylenesulfide, and copolyesters, among other non-compliant materials. Additionally, the cooling balloon can also be formed from a compliant material. Examples of non-compliant materials include, but are not limited to, nylon, and polyamines, among other compliant materials. Other balloon materials may also be used.

Figure 3:
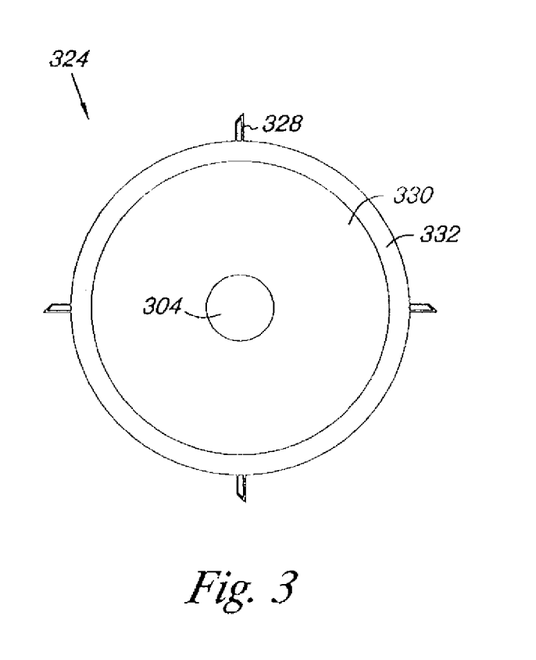
FIG. 3 illustrates a cross-sectional view of the catheter device 100 illustrated in FIG. 1 taken along lines 3-3.

FIG. 3 illustrates a cross-sectional view of the catheter device illustrated in FIG. 1 taken along lines 3-3. For one or more of the embodiments, the infusion device 326 delivers the anesthetic fluid to the perivenous location to desensitize the nerves of the vein to provide pain relief while the energy delivery device delivers energy to the vein. As seen in FIG. 3, the at least one needle 328 is in fluid communication with a chamber 332 to deliver the anesthetic fluid to the perivenous location. The infusion device 324 can include the infusion balloon 330 that can be inflated to increase the pressure from the needle 328 on the vein.

Figure 4A:
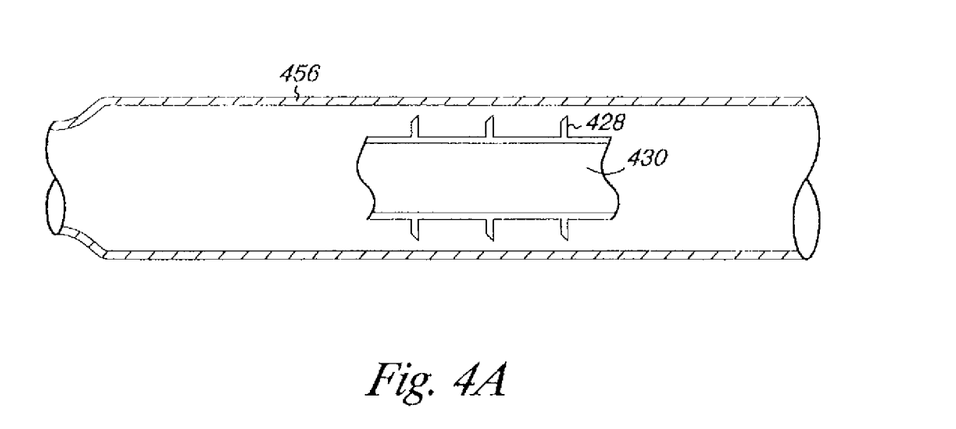
FIGS. 4A-4C illustrates a cross-sectional view of the profile of the catheter device illustrated in FIG. 1 taken along lines 4-4.
Figure 4B:
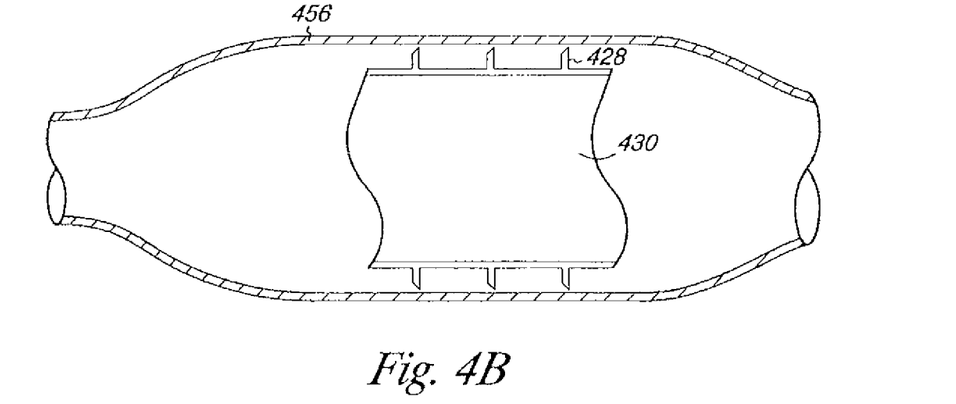
Figure 4C:
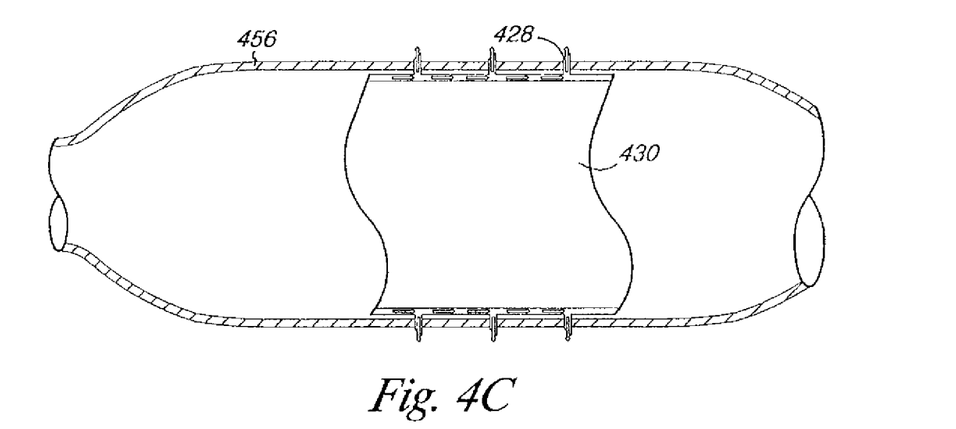

FIGS. 4A-4C illustrates a cross-sectional view of the profile of the catheter device illustrated in FIG. 1 taken along lines 4-4. As seen in FIGS. 4A-4C, the infusion device 426 changes from an un-expanded state (FIG. 4A) to an intermediate expanded state (FIG. 4B). Additionally, the infusion device 426 changes from the intermediate expanded state (FIG. 4B) to the expanded state (FIG. 4C)

As the anesthetic fluid is delivered to the infusion balloon 430, the infusion balloon 430 changes from the un-expanded state (FIG. 4A) to the intermediate expanded state (FIG. 4B). At the intermediate expanded state, the force exerted by the needle 428 against the vein 456 can stretch the vein 456, as seen in FIG. 4B. FIG. 4C illustrates the expanded state of the infusion balloon 430 where the force exerted by the needle 428 has punctured the vein 456. Once the vein 456 is punctured, the anesthetic fluid can be delivered to the perivenous location via the chamber 432, which is in fluid communication with the needle 428.

Depending on the particular vein being treated, an expanded state diameter of the infusion balloon 430 can vary. For example, some veins can stretch approximately 6 millimeters (mm) to 8 mm. Thus, the infusion balloon 430 can have an expanded state diameter that is at least 6 mm greater than the initial diameter of the particular vein being treated. The needle 428 can have a length within a range of from 0.1 mm to 3.0 mm. In embodiments, the length of the needle 428 is within a range of from 0.5 mm to 1.0 mm. Additionally, an inner diameter of the needle 428 can be within a range of 100 micrometers (μm) to 500 μm.

For one or more embodiments, the needle can be formed from stainless steel, 316 stainless steel, MP35N®, elgiloy, platinum, iridium, aluminum oxide, ruby, sapphire, titanium, and combinations thereof. Additional materials may also be used to form the needle.

For one or more embodiments, the infusion balloon can be formed from a suitable balloon material, as discussed herein regarding the cooling balloon. For example, the infusion balloon can be formed from semi-compliant material, non-compliant material, and other balloon materials.

For the embodiments, the anesthetic fluid can be selected from fluids that have anesthetic and/or vaso-spasming characteristics. Examples of the anesthetic fluid include, but are not limited to, fluids such as lidocaine, hypertonic saline, sclerosing agents, and combinations thereof. In one embodiment, the vaso-spasm fluids can include a mixture of 1% Sotradecol® or polidocanol. The induced vaso-spasm can cause the vein to constrict, which can assist decreasing the initial diameter of the vein.

Anesthetic fluids are used to desensitize the nerves of the vein and provide pain relief while the energy delivery device is delivering energy to the vein. For one or more embodiments, a mixture of 100 cubic centimeters (cc) to 200 cc of 5% lidocaine with epinephrine can be used. Other mixtures can be used as well. While the anesthetic fluid is delivered to the perivenous location, the infusion balloon can begin to return to the un-expanded state as the vein may spasm and start to constrict.

Figure 5:
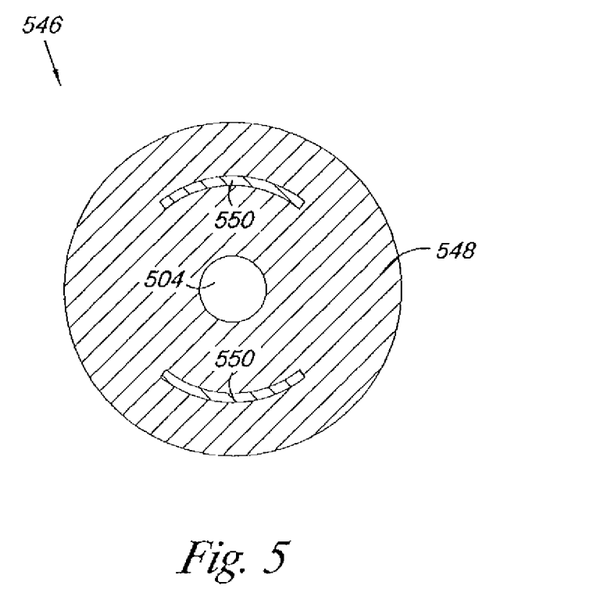
FIG. 5 illustrates a cross-sectional view of the catheter device illustrated in FIG. 1 taken along lines 5-5.

FIG. 5 illustrates a cross-sectional view of the catheter device illustrated in FIG. 1 taken along lines 5-5. For the various embodiments, the energy delivery device 546 may have a number different profiles, cross-sectional shapes, and/or dimensions along the length of the energy delivery device 546. For example, the energy delivery device 546 can have a cross-section shape that includes, but is not limited to, a circle, oval, square, triangle, trapezoid, polygon, parallelogram, rhombus, and other shapes. The various shapes can help assist the closure of the vein as the diameter beings to decrease as the energy is delivered to the vein.

As seen in FIG. 5, the body portion 548 of the energy delivery device 546 has a circular cross-section and includes the one or more electrodes 550. As discussed herein, additional electrodes 550 may be added to the body portion 548. The electrodes 550 can be formed from conductive strips, plates, wires, and combinations thereof. In one embodiment, the electrodes 550 are made from stainless steel. As seen in FIG. 5, the electrodes 550 are conductive metal strips completely embedded into the body portion 548 of the energy delivery device 546. The body portion 548 can be formed from polymers and/or other non-conductive materials. In additional embodiments, the body portion can be a wire mesh expander where the electrodes are mounted on the wire mesh expander.

Depending on the configuration of the electrodes 550, the electrodes 550 can be operated in bipolar or monopolar configuration. For example, one electrode can be in coupled electrically to a positive terminal of the RF generator thus giving that electrode a "+" polarity. Another electrode can be electrically coupled to a negative terminal of the bipolar RF generator giving that electrode a "−" polarity. The RF generator can be controlled by a microprocessor in response to external commands or to data from a sensor.

Figure 6:
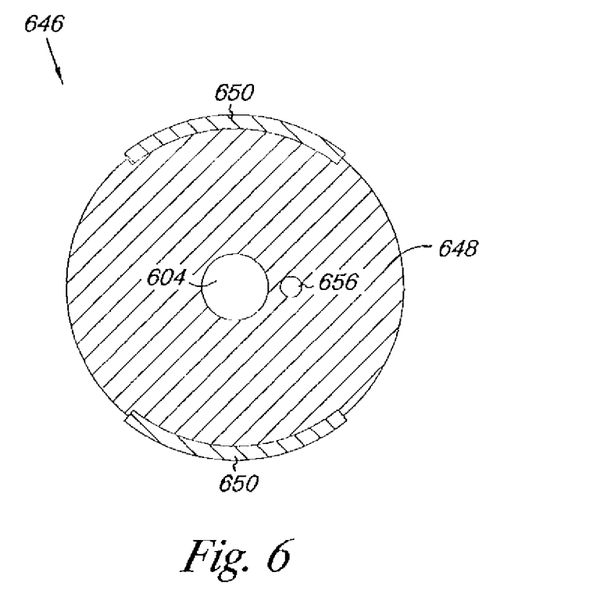
FIG. 6 illustrates additional cross-sectional views of the catheter device illustrated in FIG. 1 taken along lines 5-5.

FIG. 6 illustrates an additional cross-sectional view of the catheter device illustrated in FIG. 1 taken along lines 5-5. In this embodiment, the electrodes 650 can be partially embedded in the body portion 648 and protrude slightly from the surface of the body portion 648 of the energy delivery device 646. Additionally, as seen in FIG. 6, the energy delivery device 646 can include a temperature sensor 656, such as a thermocouple, located between the electrodes 650 to monitor the temperature of the vein being treated.

Monitoring the temperature of the vein can provide an indication of when the initial diameter of the vein is about to begin to collapse. For example, collagen fibrils of veins can shrink at approximately 70° C. or higher. Additionally, temperatures greater than 85° C. begin to produce heat-induced coagulum, which can collect on the electrodes. Thus, maintaining the temperature of the vein between 70° C. to 85° C. can decrease the diameter of the vein without forming the coagulum. The temperature sensor can produce signals that are input to a microprocessor of the power supply, which can control the energy delivered to the electrodes in accordance with the monitored temperature. In one embodiment, blood can be displaced from the vein prior to delivering energy to the vein to help minimize coagulum buildup on the electrodes.

Besides temperature sensors, additional methods for monitoring the collapsing vein can be used. For example, ultrasonic piezoelectric elements that emit pulsed ultrasound waves can be used. Additionally, optical coherence tomography, optoacoustic imaging, and microwave thermography, can be used.

Figure 7A:
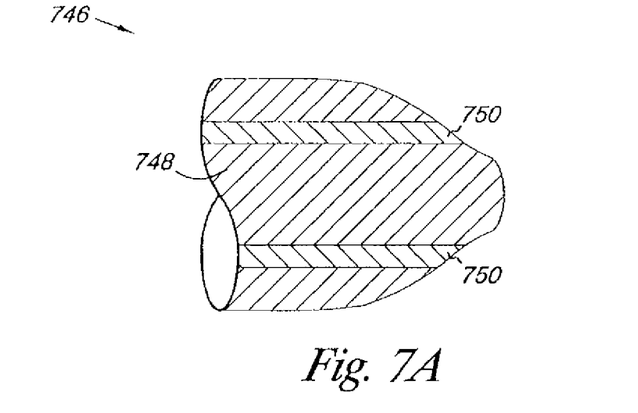
FIG. 7A-7C illustrates additional profiles of the catheter device illustrated in FIG. 1 taken along lines 7-7.
Figure 7B:
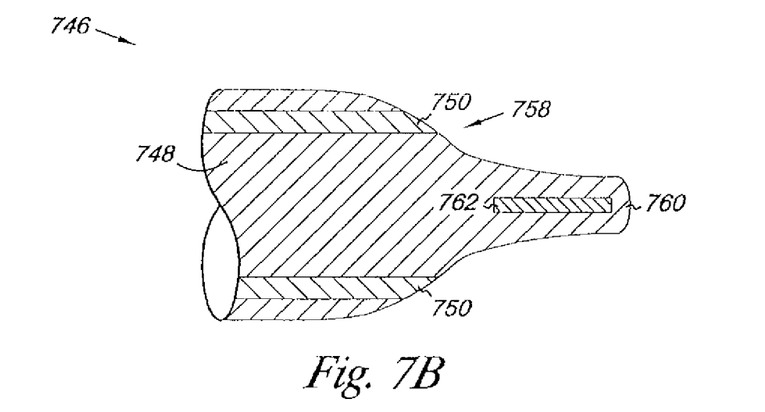
Figure 7C:
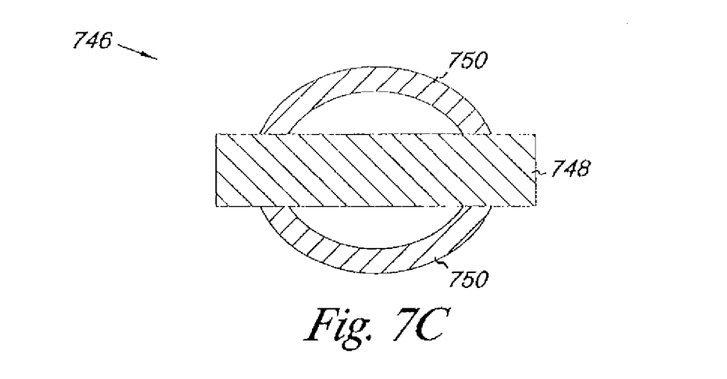

Moreover, the profile of the energy delivery device can vary. For example, the profile and shape of the energy delivery device can vary to assist collapsing the vein. FIG. 7A-7C illustrates additional profiles of the catheter device illustrated in FIG. 1 taken along lines 7-7. As seen in FIG. 7A, the profile of the body portion 748 of the energy delivery device 746 can be tapered, where the electrodes 750 are embedded in the body portion 748 of the energy delivery device 746.

As seen in FIG. 7B, the body portion 748 of the energy delivery device 746 can include a tapered portion 758 and a wire portion 760 that extends outward. The embodiment in FIG. 7B also includes one or more electrodes 762 positioned along the wire portion 760. The electrodes 750 positioned in the tapered portion 758 can be used to begin collapsing the vein. Once the vein has begun to collapse, the energy delivery device 746 can be retracted such that the one or more electrodes 762 positioned in the wire portion 760 can be used to deliver additional energy to the partially collapsed vein, which can help further collapse the vein.

As seen in FIG. 7C, the electrodes 750 can be bowed and extend from the body portion 748. For one embodiment, the electrodes 750 can be collapsible to help accommodate the collapsing vein.

Figure 8:
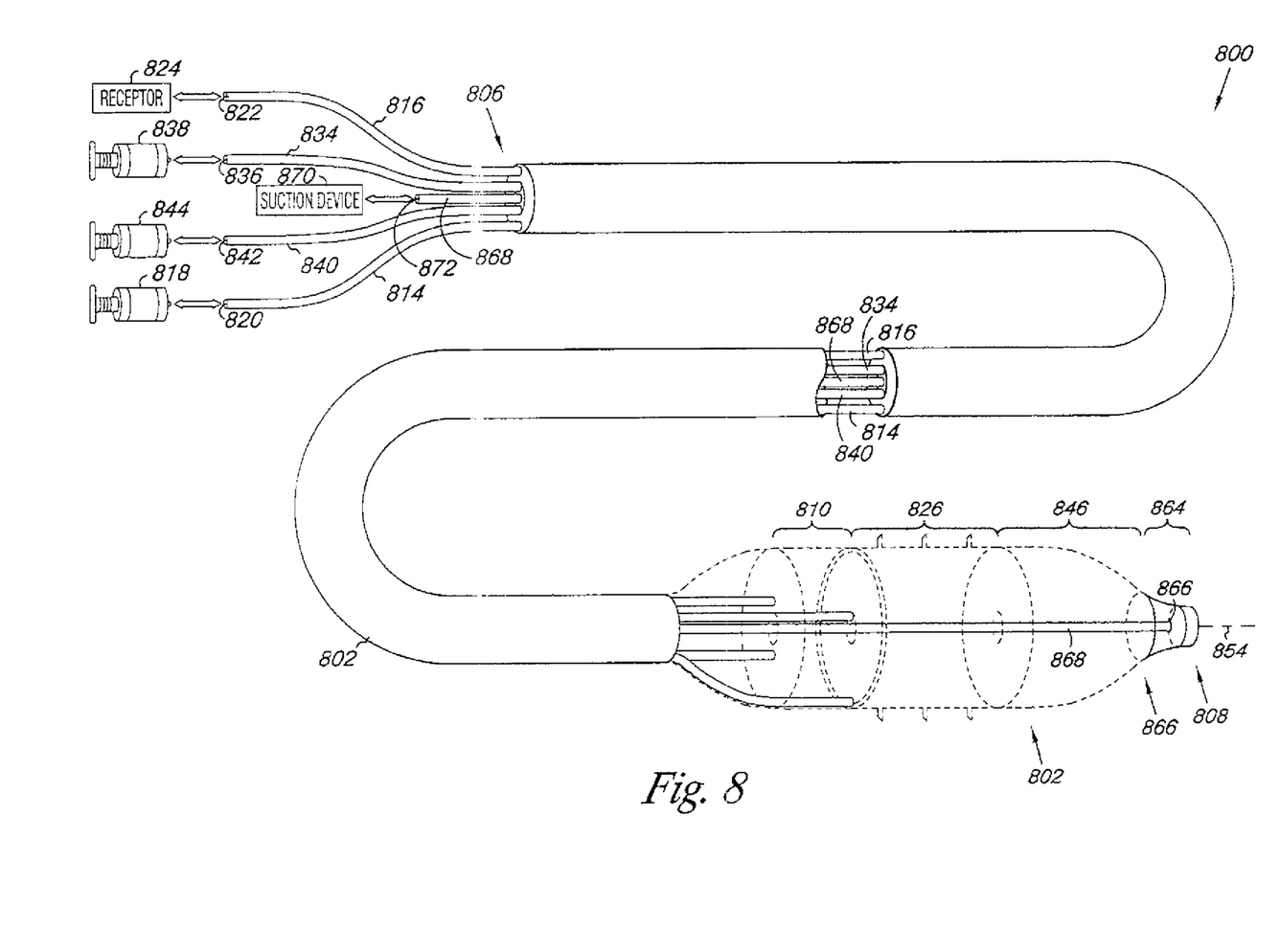
FIG. 8 illustrates an embodiment of the catheter device according to the present disclosure.

FIG. 8 illustrates an embodiment of the catheter device of the present disclosure. For one or more embodiments, the catheter device 800 includes a suction delivery device 864 coupled to the elongate body 802. The suction delivery device 864 has a suction port 866 and is in fluid communication with a suction lumen 868. The suction port 866 can be located between the distal end 808 of the elongate body 802 and the energy delivery device 846 such that as the diameter of the vein is decreasing due to the delivered energy, the suction delivery device 864 can assist the collapsing vein. For example, the suction lumen 868 couples a suction device 870 to the suction port 866 to apply a vacuum to the vein. The suction device 870 is releasably coupled to the catheter device 800, e.g. a port 872. Examples of the suction device include, but are not limited to, wall suction, a suction syringe or small suction pump.

As seen in FIG. 8, the cooling device 810, infusion device 826, and energy delivery device 846 are positioned sequentially along the longitudinal axis 854 of the elongate body 802. For the various embodiments, the catheter device 800 can be advanced in a stepwise manner along the vein, where each device is used to treat the vein. For example, the cooling device 810 can be used to reduce the temperature of the vein. The catheter device 800 can be retracted such that the infusion device 826 is aligned with the portion of the vein that has the reduced temperature and deliver the anesthetic fluid to the perivenous location. The catheter device 800 can be further retraced such that the energy delivery device 846 is aligned with the portion of the vein that has been treated with the anesthetic fluid and deliver energy to the vein to collapse the vein and potentially remove the vein from circulation.

However, for one or more embodiments, the elongate body can have two or more devices located in the same region. Having two or more devices at the same region allows the devices to treat a segment of the vein without advancing the catheter device stepwise along the vein after each device is used to treat the vein.

Figure 9:
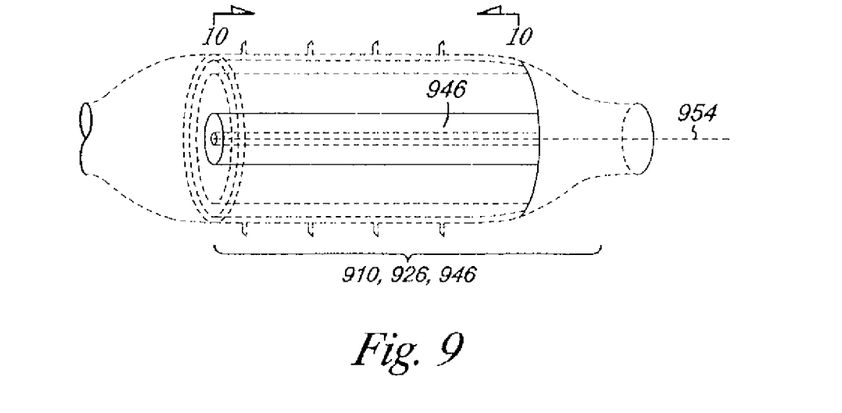
FIG. 9 illustrates an embodiment of the catheter device according to the present disclosure.

FIG. 9 illustrates an embodiment of the catheter device according to the present disclosure. As seen in FIG. 9, the cooling device 910, infusion device 926, and energy delivery device 946 are positioned within the same region of the elongate body 902. In this embodiment, the cooling device 910, infusion device 926, and the energy delivery device 946 are positioned coaxially around the longitudinal axis 954.

Figure 10:
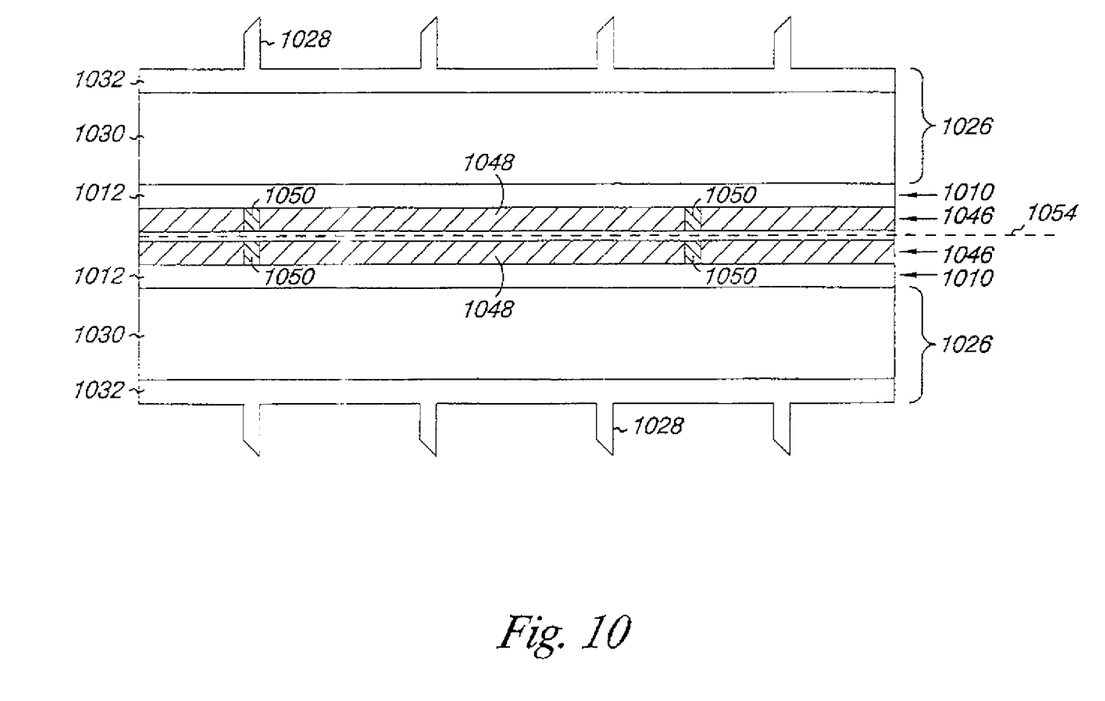
FIG. 10 illustrates a profile of the catheter device illustrated in FIG. 9 taken along lines 10-10.

FIG. 10 illustrates a profile of the catheter device illustrated in FIG. 9 taken along lines 10-10. As seen in FIG. 10, the energy delivery device 1046 extends along the longitudinal axis 1054. The energy delivery device 1046 includes one or more electrodes 1050 embedded in the body portion 1048 of the energy delivery device 1046. Additional pairs of electrodes can be used along the length of the body portion 1048 of the energy delivery device 1046. The cooling device 1010 includes the cooling balloon 1012 positioned coaxially around the energy delivery device 1046. The infusion device 1026 is positioned coaxially around the cooling device 1010. For the embodiments, the needle 1028 is in fluid communication with the chamber 1032 and the infusion balloon 1030 is inflated to puncture the vein with the needle 1028.

In embodiments, the cooling device can be combined with the infusion device. For example, the infusion balloon can be inflated to the intermediate state using the cooling fluid. For the various embodiments, the infusion balloon can be held at the intermediate state for a predetermined amount of time to decrease the temperature of the vein. Once the vein temperature has decreased, the infusion balloon can continue to inflate to the expanded state where the at least one needle can puncture the vein and the anesthetic fluid is delivered to the perivenous location.

FIG. 11 provides a system of the present disclosure. For the various embodiments, the system includes a catheter device 1100 that includes the cooling device 1110, the infusion device 1126, the energy delivery device 1146, and a monitoring device 1174. For the embodiments, the monitoring device 1174 includes a stimulation electrode 1176 and a sensing electrode 1178 that are spaced axially apart. The materials and operation of the cooling device 1110, infusion device 1126, and energy delivery device 1146 are similar to that described herein with regards to FIG. 1.

As seen in FIG. 11, the monitoring device 1174 includes the stimulation electrode 1176 and the sensing electrode 1178 to monitor nerve sensitivity of the nerves in the vein. After the anesthetic fluid delivered to the perivenous location via the infusion device 1126 the nerve sensitivity can decrease and can be monitored by the monitoring device 1174. Additionally, the monitoring device 1174 can be used to determine the sensitivity of the nerves while the temperature of the vein is decreased by the cooling device 1110. For one or more embodiments, the monitoring device 1174 can be used simultaneously with the cooling device 1110 and/or the infusion device 1126 to monitor the sensitivity of the nerves in the vein. One skilled in the art can appreciate at what level of sensitivity the nerves will be desensitized to minimize the pain felt by the patient.

For one or more embodiments, the stimulation electrode 1176 and the sensing electrode 1178 can be positioned on opposite ends of the infusion device 1126. In an additional embodiment, the stimulation and sensing electrodes 1176, 1178 can be positioned on opposite ends of the cooling device 1110. Moreover, the monitoring device 1174 can be located at other positions along the catheter device 1100.

The stimulation electrode 1176 and the sensing electrode 1178 can be patches, strips, circumferential bands, and wires, among other structures. As seen in FIG. 11, the stimulation electrode 1176 and the sensing electrode 1178 are strips. For one or more embodiments, the stimulation electrode 1176 and the sensing electrode 1178 can be mounted on a wire mesh expander 1184. The wire mesh expander 1184 can expand and/or contract with the infusion device 1126 and/or cooling device 1110.

For the embodiments, the stimulation electrode 1176 is electrically coupled to a signal generator 1186 via a wire 1188. The signal generator 1186 can generate signals that are received by the stimulation electrode 1176 that can be used to stimulate the nerves in the vein. The sensing electrode 1178 monitors the electrical activity, i.e., nerve transmission, of the nerves. The nerve transmissions can change as varying levels of the anesthetic fluid are introduced to the perivenous location and the nerves become desensitized. Additionally, nerve transmissions can change as the temperature of the vein decreases. The sensing electrode 1178 is electrically coupled to a monitoring unit 1190 via a wire 1192, which processes data received from the sensing electrode 1178. The sensing electrode 1178 measures the nerve transmission via electrical activity of the nerves. For one or more embodiments, the monitoring device 1174 is advantageous because it can be used to monitor the nerve sensitivity such that the pain felt by the patient is minimized.

In other embodiments, the monitoring device can include mounting the stimulation and sensing electrodes on a balloon. Furthermore, with an appropriate distance between the stimulation and sensing electrodes and an appropriate signal strength from the signal generator, the stimulation and sensing electrodes do not contact the vein because electrical signals can be transmitted through blood. For one embodiment, the needle(s) of the infusion device can be electrically coupled to the signal generator and monitoring unit and used as the monitoring device to monitor the effect of the anesthetic fluid simultaneously as the anesthetic fluid is being delivered to the perivenous location. Additionally, in one embodiment, the at least one needle can also be configured to delivery energy to the vein. For example, a predetermined number of the plurality of needles can be electrically coupled to the power supply to delivery energy to the vein.

In an additional embodiment, the monitoring device can include only the stimulation electrode, where the stimulation electrode is electrically coupled to a signal generator via a wire. In this embodiment, the signal generator can generate signals of different strengths and deliver the signals to the vein via the stimulation electrode. After each signal is delivered to the vein, the patient can be asked whether or not they felt pain. The operator, based on experience, can determine from the patient's response whether or not additional anesthetic fluid should be delivered to vein to minimize the pain felt by the patient.

For one or more embodiments, the cooling device 1110, infusion device 1126, and the energy delivery device 1146 can be positioned sequentially along the longitudinal axis 1154, as seen in FIG. 11. Additionally, the cooling device, infusion device, and the energy delivery device can be positioned coaxially as described with reference to FIG. 9. The cooling device 1110 includes the cooling balloon 1112 and the inflow lumen 1114 and the outflow lumen 1116 to circulate the cooling fluid. The cooling balloon 1112 is in fluid communication with the inflow lumen 1114 to receive the cooling fluid from the inflation device 1122. For the various embodiments, the inflow lumen 1114 couples the inflation port 1120 to the expandable volume defined at least in part by the cooling balloon 1112 of the cooling device 1110. For the various embodiments, the cooling balloon 1112 is in fluid communication with the outflow lumen 1116 to remove the cooling fluid from the cooling balloon 1112. For the various embodiments, the outflow lumen 1116 couples the port 1124 to the receptacle 1126 that collects the circulated cooling fluid.

For one or more embodiments, the infusion device 1126 includes the plurality of needles 1128 that can puncture the vein to deliver an anesthetic fluid to the perivenous location. The infusion device 1126 includes the infusion balloon 1130 and the chamber 1132.

For one or more embodiments, and as seen in FIG. 11, the energy delivery device 1146 includes the body portion 1148 and one or more electrodes 1150. For the various embodiments, the electrodes 1150 are electrically coupled to the power supply 1194, e.g. an RF generator, to deliver energy to the vein. For example, one electrode 1150 can be electrically coupled to the power supply 1194 via a wire 1196 and the other electrode 1150 can be electrically coupled to the power supply 1194 via a wire 1198.

An additional embodiment of the present disclosure includes an ablation catheter including the energy delivery device and the monitoring device. In this embodiment, the monitoring device of the present invention can be used separately from the cooling device and the infusion device and in conjunction with the energy delivery device. For example, the monitoring device can be mounted on the ablation catheter that is used to delivery energy to a vein. In this embodiment, the ablation catheter can include only the energy delivery device and the monitoring device as disclosed herein.

For one or more embodiments, the catheter device can include one or more areas, bands, coatings, and/or members that are detectable by imaging modalities such as X-Ray, MRI, ultrasound, and fluoroscopy, among other imaging techniques. In some embodiments at least a portion of the elongate body is at least partially radiopaque.

Embodiments of the present disclosure can further include methods of forming the catheter device. For one or more embodiments, the method includes providing an elongate body having a lumen. The method can include coupling a cooling device including a cooling balloon that is in fluid communication with an inflow lumen and an outflow lumen to the elongate body. An infusion device including a chamber and at least one needle can be coupled to the elongate body, where the at least one needle is in fluid communication with the chamber. Additionally, an energy delivery device including one or more electrodes can be coupled to the elongate body. For one or more embodiments, the method can include embedding or partially embedding the one or more electrodes in a body portion of the energy delivery device.

For one embodiment, the method further includes integrating a monitoring device with the elongate body, where the monitoring device includes a stimulation electrode and a sensing electrode. Integrating the monitoring device can include mounting the stimulation electrode and the sensing electrode on a wire mesh expander element and positioning the stimulation electrode at a proximal end of the infusion device and positioning the sensing electrode at a distal end of the infusion device. The methods can include mounting the stimulation electrode and sensing electrode on opposite sides of the cooling device.

The catheter device can be advanced such that the cooling device is aligned with the farthest portion of the vein receiving treatment. As one skilled in the art will appreciate, the catheter device can be positioned in a predetermined position in various ways, as described herein. The elongate body can be constricted to the un-expanded state by the presence of a retractable sheath positioned adjacent the distal end of a delivery catheter.

A retractable sheath can be positioned over the entire elongate body while the catheter is being positioned at the predetermined position. The retractable sheath can move longitudinally along the elongate body. Once the retractable sheath is retracted, each device, i.e., the cooling device, the infusion device, energy thermal device, and the monitoring device, can be used, individually or simultaneously. For one or more embodiments, the retractable sheath can be used to assist in collapsing the needles and the infusion balloon as the elongate body is advanced within the vein.

The catheter device, as discussed herein, can be positioned at the predetermined vascular location of patient using minimally invasive percutaneous, transluminal techniques. For example, a guide wire can be positioned within the vascular system of a patient at the predetermined vascular location. The catheter device of the present disclosure can be positioned over the guide wire and the elongate body can be advanced so as to position the cooling balloon at the predetermined location.

The guide wire is preferably insulated so as to prevent or help minimize any coupling effect the electrodes may have on the guide wire. Once the elongate body is positioned at the predetermined location, the guide wire can be removed before the energy delivery device is activated.

At the predetermined location, the catheter device can be used to treat the vein. For example, the cooling device can reduce the temperature of the vein by inflating the cooling balloon with the cooling fluid. The cooling balloon in the expanded state is in contact with the vein for a predetermined amount of time. The predetermined amount of time will vary depending on various factors, e.g. desired temperature of the vein, flow rate of cooling fluid, temperature of the cooling fluid, etc.

The cooling balloon can be deflated and the catheter device can be retracted to align the portion of the vein that has the reduced temperature with the infusion device. The infusion device can then be used to deliver the anesthetic fluid to the perivenous location by piercing the vein with the plurality of needles by inflating the infusion balloon. After the anesthetic fluid has been delivered to the perivenous location, the infusion balloon can be deflated and the catheter device can be retracted to align the energy delivery device with the portion of the vein that has the anesthetic fluid at the perivenous location. Thus, the treatment of the vein can consist of a sequence of treatments including reducing the vein temperature, delivering the anesthetic fluid, and applying energy to the vein.

Applying energy to the vein via the energy delivery device causes the original diameter of the vein to decrease and can potentially be removed from circulation. For example, an RF generator can be activated to supply RF energy to the one or more electrodes. The thermal effect from the RF energy can produce structural transfiguration of the collagen fibrils in the vein and the initial diameter of the vein is decreased and potentially removes the vein from circulation.

Additionally, the monitoring device can be used to monitor the nerve transmissions of the nerves of the vein. The stimulation electrode can receive a signal from the signal generator to stimulate nerves in the vein. The sensing electrode can receive electrical activity of the stimulated nerves and sends the monitored electrical activity to the monitoring unit to determine the sensitivity of the nerves. The electrical activity of the nerves can be affected from various levels of the anesthetic fluid. Additionally, reducing the temperature of the vein will affect the electrical activity of the nerves. Thus, the monitoring device can be used to determine the sensitivity of the nerves such that the pain felt by the patient is minimized.

While the present disclosure has been shown and described in detail above, it will be clear to the person skilled in the art that changes and modifications may be made without departing from the spirit and scope of the disclosure. As such, that which is set forth in the foregoing description and accompanying drawings is offered by way of illustration only and not as a limitation. The actual scope of the disclosure is intended to be defined by the following claims, along with the full range of equivalents to which such claims are entitled. In addition, one of ordinary skill in the art will appreciate upon reading and understanding this disclosure that other variations for the disclosure described herein can be included within the scope of the present disclosure.

In the foregoing Detailed Description, various features are grouped together in several embodiments for the purpose of streamlining the disclosure. This method of disclosure is not to be interpreted as reflecting an intention that the embodiments of the disclosure require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A catheter device for delivering energy to a vein, comprising:
   an elongate body;
   a cooling device coupled to and distal of the elongate body to reduce a temperature of the vein;
   an infusion device coupled to and distal of the cooling device, the infusion device including at least one needle to puncture the vein; and
   an energy delivery device coupled to and distal of the infusion device, the energy delivery device including one or more electrodes to deliver energy to the vein.

2. The catheter device of claim 1, where the cooling device includes a cooling balloon and an inflow lumen, where the inflow lumen is in fluid communication with the cooling balloon to deliver a cooling fluid to the cooling balloon.

3. The catheter device of claim 2, where the cooling device includes an outflow lumen in fluid communication with the cooling balloon to remove the cooling fluid from the cooling balloon.

4. The catheter device of claim 1, where the infusion device includes an inflation balloon and a chamber, where the chamber is in fluid communication with the at least one needle to deliver an anesthetic fluid to a perivenous location.

5. The catheter device of claim 1, the energy delivery device is positioned adjacent a distal end of the elongate body, the infusion device is positioned adjacent the energy delivery device, and the cooling device is positioned adjacent the energy delivery device.

6. The catheter device of claim 1, where the energy delivery device includes a body portion, where the one or more electrodes are partially embedded in the body portion.

7. The catheter device of claim 1, where the energy delivery device is positioned along a longitudinal axis of the elongate body.

8. The catheter device of claim 7, where the cooling device is positioned coaxially around the energy delivery device and the infusion device is positioned coaxially around the cooling device.

9. The catheter device of claim 1, further including a suction delivery device including a suction port positioned adjacent a distal end of the elongate body and a suction lumen in fluid communication with the suction port, where the suction lumen couples a suction device to the suction port to apply a vacuum to the vein.

10. A system, comprising:
    an elongate body having a lumen;
    a cooling device coupled to and distal of the elongate body including a cooling balloon, an inflow lumen, and an outflow lumen, where the inflow lumen and the outflow lumen are both in fluid communication with the cooling balloon;
    an infusion device coupled to and distal of the cooling device, the infusion device including an infusion balloon, a chamber, and at least one needle, where the at least one needle is in fluid communication with the chamber;
    an energy delivery device coupled to and distal of the infusion device, the energy delivery device including at least one electrode, where the at least one electrode is electrically coupled to a power supply to deliver energy to the vein; and a monitoring device integrated with the elongate body including a stimulation electrode and a sensing electrode to monitor electrical activity of nerves in the vein.

11. The system of claim 10, where the stimulation electrode and the sensing electrode are spaced axially apart.

12. The system of claim 10, where the stimulation electrode and the sensing electrode are positioned on opposite ends of the infusion device.

13. The system of claim 10, where the stimulation electrode and the sensing electrode are mounted on a wire mesh expander element.

14. The system of claim 10, further including a signal generator electrically coupled to the stimulation electrode.

15. The system of claim 10, further including a monitoring unit electrically coupled to the sensing electrode.

16. The system of claim 10, where the power supply electrically coupled to the one or more electrode is a radiofrequency generator.

17. A method of forming a catheter device, comprising:
providing an elongate body having a lumen;
coupling a cooling device to and distal of the elongate body, the cooling device including a cooling balloon that is in fluid communication with an inflow lumen and an outflow lumen;
coupling an infusion device to and distal of the cooling device, the infusion device including a chamber and at least one needle to the elongate body, where the at least one needle is in fluid communication with the chamber; and
coupling an energy delivery device to and distal of the infusion device, the energy delivery device including a body portion and one or more electrodes.

18. The method of claim 17, further including partially embedding the one or more electrode into the body portion of the energy delivery device.

19. The method of claim 17, further including integrating a monitoring device with the elongate body, where the monitoring device includes a stimulation electrode and a sensing electrode.

20. The catheter device of claim 19, where integrating the monitoring device includes mounting the stimulation electrode and the sensing electrode on a wire mesh expander element and positioning the stimulation electrode at a proximal end of the infusion device and positioning the sensing electrode at a distal end of the infusion device.

* * * * *